(12) United States Patent
Fox et al.

(10) Patent No.: US 7,241,593 B2
(45) Date of Patent: Jul. 10, 2007

(54) MATERIALS AND METHODS FOR PREPARING DIMERIC GROWTH FACTORS

(75) Inventors: Brian A. Fox, Seattle, WA (US); Margaret Dow Moore, Seattle, WA (US); Kristine M. Swiderek, Woodinville, WA (US); Carl W. Birks, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 415 days.

(21) Appl. No.: 10/365,095

(22) Filed: Feb. 11, 2003

(65) Prior Publication Data

US 2003/0224488 A1 Dec. 4, 2003

Related U.S. Application Data

(60) Provisional application No. 60/355,882, filed on Feb. 11, 2002.

(51) Int. Cl.
*C12P 21/04* (2006.01)
*C07K 14/49* (2006.01)

(52) U.S. Cl. ................ 435/69.7; 530/350; 530/399

(58) Field of Classification Search ............ None
See application file for complete search history.

(56) References Cited

U.S. PATENT DOCUMENTS

| | | | |
|---|---|---|---|
| 5,073,627 A | 12/1991 | Curtis et al. ............ 530/351 |
| 5,674,712 A | 10/1997 | Grandi et al. ........... 435/69.6 |
| 5,705,484 A | 1/1998 | Thomason ............... 514/12 |
| 5,935,815 A | 8/1999 | van de Ven et al. ..... 435/69.1 |
| 6,018,026 A | 1/2000 | Sledziewski et al. ..... 530/350 |
| 6,495,668 B1 | 12/2002 | Gilbert et al. .......... 530/399 |
| 6,706,687 B1 | 3/2004 | Eriksson et al. ........ 514/12 |
| 2003/0049816 A1 | 3/2003 | Baker et al. ............ 435/183 |
| 2003/0109000 A1 | 6/2003 | Moore et al. ........... 435/69.1 |

FOREIGN PATENT DOCUMENTS

| | | |
|---|---|---|
| WO | 98/49311 | 11/1998 |
| WO | 00/61768 | 10/2000 |
| WO | 01/40466 A2 | 6/2001 |
| WO | 01/55430 | 8/2001 |
| WO | WO 02/072607 | 9/2002 |
| WO | WO 02/081520 | 10/2002 |
| WO | WO 03/010202 | 2/2003 |
| WO | 03/072753 A2 | 9/2003 |

OTHER PUBLICATIONS

Fischer, M., et al., *Nature Biotechnology* 15:142-145, 1997.
Uutela, M., et al., *Circulation* 103:2242-2247, 2001.
LaRochelle, W., et al., *Nature Cell Biology* 3:517-521, 2001.
Hu, S., et al., *Cancer Research* 56:3055-3061, 1996.
Pantoliano, M., et al., *Biochemistry* 30(42):10117-10125, 1991.
Bergsten et al., Nature Cell Biol. 3:512-516, 2001.

*Primary Examiner*—Marianne P. Allen
(74) *Attorney, Agent, or Firm*—Gary E. Parker

(57) ABSTRACT

Proteins consisting of, from amino to carboxyl terminus, a first PDGF-D growth factor domain polypeptide, a linker polypeptide, and a second PDGF-D growth factor domain polypeptide, and materials and methods for making the proteins are disclosed. Each of the first and second PDGF-D growth factor domain polypeptides consists of a sequence of amino acid residues as shown in SEQ ID NO:2 or SEQ ID NO:4 from amino acid x to amino acid y, wherein x is an integer from 246 to 258, inclusive, and y is an integer from 365–370, inclusive. The linker polypeptide consists of from 11–40 amino acid residues. The proteins can be used to stimulate the production of bone and/or connective tissue in both humans and non-human animals.

14 Claims, No Drawings

SEQUENCE LISTING

<160> NUMBER OF SEQ ID NOS: 34

<210> SEQ ID NO 1
<211> LENGTH: 1882
<212> TYPE: DNA
<213> ORGANISM: Homo sapiens
<220> FEATURE:
<221> NAME/KEY: CDS
<222> LOCATION: (226)...(1338)

<400> SEQUENCE: 1

```
ccgtcaccat ttatcagctc agcaccacaa ggaagtgcgg cacccacacg cgctcggaaa      60
gttcagcatg caggaagttt ggggagagct cggcgattag cacagcgacc cgggccagcg     120
cagggcgagc gcaggcggcg agagcgcagg gcggcgcggc gtcggtcccg ggagcagaac     180
ccggcttttt cttggagcga cgctgtctct agtcgctgat cccaa atg cac cgg ctc     237
                                                  Met His Arg Leu
                                                    1 atc ttt gtc tac act cta atc tgc gca aac ttt tgc agc tgt cgg gac      285
Ile Phe Val Tyr Thr Leu Ile Cys Ala Asn Phe Cys Ser Cys Arg Asp
  5                  10                  15                  20 act tct gca acc ccg cag agc gca tcc atc aaa gct ttg cgc aac gcc      333
Thr Ser Ala Thr Pro Gln Ser Ala Ser Ile Lys Ala Leu Arg Asn Ala
             25                  30                  35 aac ctc agg cga gat gag agc aat cac ctc aca gac ttg tac cga aga      381
Asn Leu Arg Arg Asp Glu Ser Asn His Leu Thr Asp Leu Tyr Arg Arg
         40                  45                  50 gat gag acc atc cag gtg aaa gga aac ggc tac gtg cag agt cct aga      429
Asp Glu Thr Ile Gln Val Lys Gly Asn Gly Tyr Val Gln Ser Pro Arg
     55                  60                  65 ttc ccg aac agc tac ccc agg aac ctg ctc ctg aca tgg cgg ctt cac      477
Phe Pro Asn Ser Tyr Pro Arg Asn Leu Leu Leu Thr Trp Arg Leu His
 70                  75                  80 tct cag gag aat aca cgg ata cag cta gtg ttt gac aat cag ttt gga      525
Ser Gln Glu Asn Thr Arg Ile Gln Leu Val Phe Asp Asn Gln Phe Gly
 85                  90                  95                 100 tta gag gaa gca gaa aat gat atc tgt agg tat gat ttt gtg gaa gtt      573
Leu Glu Glu Ala Glu Asn Asp Ile Cys Arg Tyr Asp Phe Val Glu Val
                105                 110                 115 gaa gat ata tcc gaa acc agt acc att att aga gga cga tgg tgt gga      621
Glu Asp Ile Ser Glu Thr Ser Thr Ile Ile Arg Gly Arg Trp Cys Gly
            120                 125                 130 cac aag gaa gtt cct cca agg ata aaa tca aga acg aac caa att aaa      669
His Lys Glu Val Pro Pro Arg Ile Lys Ser Arg Thr Asn Gln Ile Lys
        135                 140                 145 atc aca ttc aag tcc gat gac tac ttt gtg gct aaa cct gga ttc aag      717
Ile Thr Phe Lys Ser Asp Asp Tyr Phe Val Ala Lys Pro Gly Phe Lys
    150                 155                 160
```

```
att tat tat tct ttg ctg gaa gat ttc caa ccc gca gca gct tca gag      765
Ile Tyr Tyr Ser Leu Leu Glu Asp Phe Gln Pro Ala Ala Ala Ser Glu
165                 170                 175                 180 acc aac tgg gaa tct gtc aca agc tct att tca ggg gta tcc tat aac      813
Thr Asn Trp Glu Ser Val Thr Ser Ser Ile Ser Gly Val Ser Tyr Asn
            185                 190                 195 tct cca tca gta acg gat ccc act ctg att gcg gat gct ctg gac aaa      861
Ser Pro Ser Val Thr Asp Pro Thr Leu Ile Ala Asp Ala Leu Asp Lys
        200                 205                 210 aaa att gca gaa ttt gat aca gtg gaa gat ctc ctc aag tac ttc aat      909
Lys Ile Ala Glu Phe Asp Thr Val Glu Asp Leu Leu Lys Tyr Phe Asn
    215                 220                 225 cca gag tca tgg caa gaa gat ctt gag aat atg tat ctg gac acc cct      957
Pro Glu Ser Trp Gln Glu Asp Leu Glu Asn Met Tyr Leu Asp Thr Pro
230                 235                 240 cgg tat cga ggc agg tca tac cat gac cgg aag tca aaa gtt gac ctg     1005
Arg Tyr Arg Gly Arg Ser Tyr His Asp Arg Lys Ser Lys Val Asp Leu
245                 250                 255                 260 gat agg ctc aat gat gat gcc aag cgt tac agt tgc act ccc agg aat     1053
Asp Arg Leu Asn Asp Asp Ala Lys Arg Tyr Ser Cys Thr Pro Arg Asn
            265                 270                 275 tac tcg gtc aat ata aga gaa gag ctg aag ttg gcc aat gtg gtc ttc     1101
Tyr Ser Val Asn Ile Arg Glu Glu Leu Lys Leu Ala Asn Val Val Phe
        280                 285                 290 ttt cca cgt tgc ctc ctc gtg cag cgc tgt gga gga aat tgt ggc tgt     1149
Phe Pro Arg Cys Leu Leu Val Gln Arg Cys Gly Gly Asn Cys Gly Cys
    295                 300                 305 gga act gtc aac tgg agg tcc tgc aca tgc aat tca ggg aaa acc gtg     1197
Gly Thr Val Asn Trp Arg Ser Cys Thr Cys Asn Ser Gly Lys Thr Val
310                 315                 320 aaa aag tat cat gag gta tta cag ttt gag cct ggc cac atc aag agg     1245
Lys Lys Tyr His Glu Val Leu Gln Phe Glu Pro Gly His Ile Lys Arg
325                 330                 335                 340 agg ggt aga gct aag acc atg gct cta gtt gac atc cag ttg gat cac     1293
Arg Gly Arg Ala Lys Thr Met Ala Leu Val Asp Ile Gln Leu Asp His
            345                 350                 355 cat gaa cga tgc gat tgt atc tgc agc tca aga cca cct cga taa        1338
His Glu Arg Cys Asp Cys Ile Cys Ser Ser Arg Pro Pro Arg *
        360                 365                 370 gagaatgtgc acatccttac attaagcctg aaagaacctt tagtttaagg agggtgagat   1398
aagagaccct tttcctacca gcaaccaaac ttactactag cctgcaatgc aatgaacaca   1458
agtggttgct gagtctcagc cttgctttgt taatgccatg gcaagtagaa aggtatatca   1518
tcaacttcta tacctaagaa ataggattg catttaataa tagtgtttga ggttatatat    1578
gcacaaacac acacagaaat atattcatgt ctatgtgtat atagatcaaa tgttttttt    1638 ttttggtata tataaccagg tacaccagag gttacatatg tttgagttag actcttaaaa   1698
tcctttgcca aaataaggga tggtcaaata tatgaaacat gtctttagaa aatttaggag   1758
ataaatttat ttttaaattt tgaaacacga aacaattttg aatcttgctc tcttaaagaa   1818
agcatcttgt atattaaaaa tcaaaagatg aggctttctt acatatacat cttagttgat   1878
tatt                                                                1882
```

<210> SEQ ID NO 2
<211> LENGTH: 370
<212> TYPE: PRT
<213> ORGANISM: Homo sapiens

<400> SEQUENCE: 2

```
Met His Arg Leu Ile Phe Val Tyr Thr Leu Ile Cys Ala Asn Phe Cys
  1               5                  10                  15

Ser Cys Arg Asp Thr Ser Ala Thr Pro Gln Ser Ala Ser Ile Lys Ala
             20                  25                  30

Leu Arg Asn Ala Asn Leu Arg Arg Asp Glu Ser Asn His Leu Thr Asp
         35                  40                  45

Leu Tyr Arg Arg Asp Glu Thr Ile Gln Val Lys Gly Asn Gly Tyr Val
 50                  55                  60

Gln Ser Pro Arg Phe Pro Asn Ser Tyr Pro Arg Asn Leu Leu Leu Thr
 65                  70                  75                  80

Trp Arg Leu His Ser Gln Glu Asn Thr Arg Ile Gln Leu Val Phe Asp
                 85                  90                  95

Asn Gln Phe Gly Leu Glu Glu Ala Glu Asn Asp Ile Cys Arg Tyr Asp
                100                 105                 110

Phe Val Glu Val Glu Asp Ile Ser Glu Thr Ser Thr Ile Ile Arg Gly
            115                 120                 125

Arg Trp Cys Gly His Lys Glu Val Pro Pro Arg Ile Lys Ser Arg Thr
        130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
        275                 280                 285

Asn Val Val Phe Phe Pro Arg Cys Leu Leu Val Gln Arg Cys Gly Gly
    290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365

Pro Arg
    370

<210> SEQ ID NO 3
<211> LENGTH: 1472
<212> TYPE: DNA
<213> ORGANISM: Mus musculus
<220> FEATURE:
<221> NAME/KEY: CDS
```

<222> LOCATION: (93)...(1205)

<400> SEQUENCE: 3

| | | | |
|---|---|---|---|
| agggactgtg cagtagaaat ccgccgactc aacccttttgg gctttattta tttactttg | | | 60 |

| | | | |
|---|---|---|---|
| gagcaacgcg atccctaggt cgctgagccc aa atg caa cgg ctc gtt tta gtc | | | 113 |
| | Met Gln Arg Leu Val Leu Val | | |
| | 1 5 | | |

| | | |
|---|---|---|
| tcc att ctc ctg tgc gcg aac ttt agc tgc tat ccg gac act ttt gcg | | 161 |
| Ser Ile Leu Leu Cys Ala Asn Phe Ser Cys Tyr Pro Asp Thr Phe Ala | | |
| 10 15 20 | | |

| | | |
|---|---|---|
| act ccg cag aga gca tcc atc aaa gct ttg cgc aat gcc aac ctc agg | | 209 |
| Thr Pro Gln Arg Ala Ser Ile Lys Ala Leu Arg Asn Ala Asn Leu Arg | | |
| 25 30 35 | | |

| | | |
|---|---|---|
| aga gat gag agc aat cac ctc aca gac ttg tac cag aga gag gag aac | | 257 |
| Arg Asp Glu Ser Asn His Leu Thr Asp Leu Tyr Gln Arg Glu Glu Asn | | |
| 40 45 50 55 | | |

| | | |
|---|---|---|
| att cag gtg aca agc aat ggc cat gtg cag agt cct cgc ttc ccg aac | | 305 |
| Ile Gln Val Thr Ser Asn Gly His Val Gln Ser Pro Arg Phe Pro Asn | | |
| 60 65 70 | | |

| | | |
|---|---|---|
| agc tac cca agg aac ctg ctt ctg aca tgg tgg ctc cgt tcc cag gag | | 353 |
| Ser Tyr Pro Arg Asn Leu Leu Leu Thr Trp Trp Leu Arg Ser Gln Glu | | |
| 75 80 85 | | |

| | | |
|---|---|---|
| aaa aca cgg ata caa ctg tcc ttt gac cat caa ttc gga cta gag gaa | | 401 |
| Lys Thr Arg Ile Gln Leu Ser Phe Asp His Gln Phe Gly Leu Glu Glu | | |
| 90 95 100 | | |

| | | |
|---|---|---|
| gca gaa aat gac att tgt agg tat gac ttt gtg gaa gtt gaa gaa gtc | | 449 |
| Ala Glu Asn Asp Ile Cys Arg Tyr Asp Phe Val Glu Val Glu Glu Val | | |
| 105 110 115 | | |

| | | |
|---|---|---|
| tca gag agc agc act gtt gtc aga gga aga tgg tgt ggc cac aag gag | | 497 |
| Ser Glu Ser Ser Thr Val Val Arg Gly Arg Trp Cys Gly His Lys Glu | | |
| 120 125 130 135 | | |

| | | |
|---|---|---|
| atc cct cca agg ata acg tca aga aca aac cag att aaa atc aca ttt | | 545 |
| Ile Pro Pro Arg Ile Thr Ser Arg Thr Asn Gln Ile Lys Ile Thr Phe | | |
| 140 145 150 | | |

| | | |
|---|---|---|
| aag tct gat gac tac ttt gtg gca aaa cct gga ttc aag att tat tat | | 593 |
| Lys Ser Asp Asp Tyr Phe Val Ala Lys Pro Gly Phe Lys Ile Tyr Tyr | | |
| 155 160 165 | | |

| | | |
|---|---|---|
| tca ttt gtg gaa gat ttc caa ccg gaa gca gcc tca gag acc aac tgg | | 641 |
| Ser Phe Val Glu Asp Phe Gln Pro Glu Ala Ala Ser Glu Thr Asn Trp | | |
| 170 175 180 | | |

| | | |
|---|---|---|
| gaa tca gtc aca agc tct ttc tct ggg gtg tcc tat cac tct cca tca | | 689 |
| Glu Ser Val Thr Ser Ser Phe Ser Gly Val Ser Tyr His Ser Pro Ser | | |
| 185 190 195 | | |

| | | |
|---|---|---|
| ata acg gac ccc act ctc act gct gat gcc ctg gac aaa act gtc gca | | 737 |
| Ile Thr Asp Pro Thr Leu Thr Ala Asp Ala Leu Asp Lys Thr Val Ala | | |
| 200 205 210 215 | | |

| | | |
|---|---|---|
| gaa ttc gat acc gtg gaa gat cta ctt aag cac ttc aat cca gtg tct | | 785 |
| Glu Phe Asp Thr Val Glu Asp Leu Leu Lys His Phe Asn Pro Val Ser | | |
| 220 225 230 | | |

| | | |
|---|---|---|
| tgg caa gat gat ctg gag aat ttg tat ctg gac acc cct cat tat aga | | 833 |
| Trp Gln Asp Asp Leu Glu Asn Leu Tyr Leu Asp Thr Pro His Tyr Arg | | |
| 235 240 245 | | |

| | | |
|---|---|---|
| ggc agg tca tac cat gat cgg aag tcc aaa gtg gac ctg gac agg ctc | | 881 |
| Gly Arg Ser Tyr His Asp Arg Lys Ser Lys Val Asp Leu Asp Arg Leu | | |
| 250 255 260 | | |

| | | |
|---|---|---|
| aat gat gat gtc aag cgt tac agt tgc act ccc agg aat cac tct gtg | | 929 |
| Asn Asp Asp Val Lys Arg Tyr Ser Cys Thr Pro Arg Asn His Ser Val | | |
| 265 270 275 | | |

| | | |
|---|---|---|
| aac ctc agg gag gag ctg aag ctg acc aat gca gtc ttc ttc cca cga | | 977 |

```
Asn Leu Arg Glu Glu Leu Lys Leu Thr Asn Ala Val Phe Phe Pro Arg
280                 285                 290                 295 tgc ctc ctc gtg cag cgc tgt ggt ggc aac tgt ggt tgc gga act gtc      1025
Cys Leu Leu Val Gln Arg Cys Gly Gly Asn Cys Gly Cys Gly Thr Val
                    300                 305                 310 aac tgg aag tcc tgc aca tgc agc tca ggg aag aca gtg aag aag tat      1073
Asn Trp Lys Ser Cys Thr Cys Ser Ser Gly Lys Thr Val Lys Lys Tyr
                315                 320                 325 cat gag gta ttg aag ttt gag cct gga cat ttc aag aga agg ggc aaa      1121
His Glu Val Leu Lys Phe Glu Pro Gly His Phe Lys Arg Arg Gly Lys
            330                 335                 340 gct aag aat atg gct ctt gtt gat atc cag ctg gat cat cat gag cga      1169
Ala Lys Asn Met Ala Leu Val Asp Ile Gln Leu Asp His His Glu Arg
        345                 350                 355 tgt gac tgt atc tgc agc tca aga cca cct cga taa aacactatgc           1215
Cys Asp Cys Ile Cys Ser Ser Arg Pro Pro Arg  *
360                 365                 370 acatctgtac tttgattatg aaaggacctt taggttacaa aaaccctaag aagcttctaa    1275
tctcagtgca atgaatgcat atggaaatgt tgctttgtta gtgccatggc aagaagaagc    1335
aaatatcatt aatttctata tacataaaca taggaattca cttatcaata gtatgtgaag    1395
atatgtatat atacttatat acatgactag ctctatgtat gtaaatagat taaatacttt    1455
attcagtata tttactg                                                   1472

<210> SEQ ID NO 4
<211> LENGTH: 370
<212> TYPE: PRT
<213> ORGANISM: Mus musculus

<400> SEQUENCE: 4

Met Gln Arg Leu Val Leu Val Ser Ile Leu Leu Cys Ala Asn Phe Ser
1               5                   10                  15

Cys Tyr Pro Asp Thr Phe Ala Thr Pro Gln Arg Ala Ser Ile Lys Ala
            20                  25                  30

Leu Arg Asn Ala Asn Leu Arg Arg Asp Glu Ser Asn His Leu Thr Asp
        35                  40                  45

Leu Tyr Gln Arg Glu Glu Asn Ile Gln Val Thr Ser Asn Gly His Val
    50                  55                  60

Gln Ser Pro Arg Phe Pro Asn Ser Tyr Pro Arg Asn Leu Leu Leu Thr
65                  70                  75                  80

Trp Trp Leu Arg Ser Gln Glu Lys Thr Arg Ile Gln Leu Ser Phe Asp
                85                  90                  95

His Gln Phe Gly Leu Glu Glu Ala Glu Asn Asp Ile Cys Arg Tyr Asp
            100                 105                 110

Phe Val Glu Val Glu Glu Val Ser Glu Ser Ser Thr Val Val Arg Gly
        115                 120                 125

Arg Trp Cys Gly His Lys Glu Ile Pro Pro Arg Ile Thr Ser Arg Thr
    130                 135                 140

Asn Gln Ile Lys Ile Thr Phe Lys Ser Asp Tyr Phe Val Ala Lys
145                 150                 155                 160

Pro Gly Phe Lys Ile Tyr Tyr Ser Phe Val Glu Asp Phe Gln Pro Glu
                165                 170                 175

Ala Ala Ser Glu Thr Asn Trp Glu Ser Val Thr Ser Ser Phe Ser Gly
            180                 185                 190

Val Ser Tyr His Ser Pro Ser Ile Thr Asp Pro Thr Leu Thr Ala Asp
        195                 200                 205
```

```
Ala Leu Asp Lys Thr Val Ala Glu Phe Asp Thr Val Glu Asp Leu Leu
    210                 215                 220
Lys His Phe Asn Pro Val Ser Trp Gln Asp Leu Glu Asn Leu Tyr
225                 230                 235                 240
Leu Asp Thr Pro His Tyr Arg Gly Arg Ser Tyr His Asp Arg Lys Ser
                    245                 250                 255
Lys Val Asp Leu Asp Arg Leu Asn Asp Val Lys Arg Tyr Ser Cys
                260                 265                 270
Thr Pro Arg Asn His Ser Val Asn Leu Arg Glu Glu Leu Lys Leu Thr
            275                 280                 285
Asn Ala Val Phe Phe Pro Arg Cys Leu Leu Val Gln Arg Cys Gly Gly
    290                 295                 300
Asn Cys Gly Cys Gly Thr Val Asn Trp Lys Ser Cys Thr Cys Ser Ser
305                 310                 315                 320
Gly Lys Thr Val Lys Lys Tyr His Glu Val Leu Lys Phe Glu Pro Gly
                325                 330                 335
His Phe Lys Arg Arg Gly Lys Ala Lys Asn Met Ala Leu Val Asp Ile
                340                 345                 350
Gln Leu Asp His His Glu Arg Cys Asp Cys Ile Cys Ser Ser Arg Pro
            355                 360                 365
Pro Arg
    370

<210> SEQ ID NO 5
<211> LENGTH: 5
<212> TYPE: PRT
<213> ORGANISM: Artificial Sequence
<220> FEATURE:
<223> OTHER INFORMATION: enterokinase cleavage site

<400> SEQUENCE: 5

Asp Asp Asp Asp Lys
1               5

<210> SEQ ID NO 6
<211> LENGTH: 4
<212> TYPE: PRT
<213> ORGANISM: Artificial Sequence
<220> FEATURE:
<223> OTHER INFORMATION: factor Xa cleavage site

<400> SEQUENCE: 6

Ile Glu Gly Arg
1

<210> SEQ ID NO 7
<211> LENGTH: 8
<212> TYPE: PRT
<213> ORGANISM: Artificial Sequence
<220> FEATURE:
<223> OTHER INFORMATION: rhinovirus 3C protease cleavage site

<400> SEQUENCE: 7

Leu Glu Val Leu Phe Gln Gly Pro
1               5

<210> SEQ ID NO 8
<211> LENGTH: 4
<212> TYPE: PRT
<213> ORGANISM: Artificial Sequence
<220> FEATURE:
```

```
<223> OTHER INFORMATION: furin cleavage site
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 3
<223> OTHER INFORMATION: Xaa = Lys or Arg

<400> SEQUENCE: 8

Arg Xaa Xaa Arg
 1

<210> SEQ ID NO 9
<211> LENGTH: 5
<212> TYPE: PRT
<213> ORGANISM: Artificial Sequence
<220> FEATURE:
<223> OTHER INFORMATION: peptide linker

<400> SEQUENCE: 9

Ser Gly Ser Gly Ser
 1               5

<210> SEQ ID NO 10
<211> LENGTH: 16
<212> TYPE: PRT
<213> ORGANISM: Artificial Sequence
<220> FEATURE:
<223> OTHER INFORMATION: peptide linker

<400> SEQUENCE: 10

Ser Gly Ser Gly Ser Ser Gly Ser Gly Ser Leu Val Pro Arg Gly Ser
 1               5                  10                  15

<210> SEQ ID NO 11
<211> LENGTH: 27
<212> TYPE: DNA
<213> ORGANISM: Artificial Sequence
<220> FEATURE:
<223> OTHER INFORMATION: oligonucleotide primer ZC38955

<400> SEQUENCE: 11
gtttccggat cataccatga ccggaag                                         27

<210> SEQ ID NO 12
<211> LENGTH: 27
<212> TYPE: DNA
<213> ORGANISM: Artificial Sequence
<220> FEATURE:
<223> OTHER INFORMATION: oligonucleotide primer ZC38602

<400> SEQUENCE: 12
cccggatcct cgaggtggtc ttgagct                                         27

<210> SEQ ID NO 13
<211> LENGTH: 69
<212> TYPE: DNA
<213> ORGANISM: Artificial Sequence
<220> FEATURE:
<223> OTHER INFORMATION: oligonucleotide primer ZC38950

<400> SEQUENCE: 13
cgaggatccg ggtcatcagg ttctgggtca tcattggtcc ctcgtggaag ctcataccat     60
gaccggaag                                                             69
```

<210> SEQ ID NO 14
<211> LENGTH: 30
<212> TYPE: DNA
<213> ORGANISM: Artificial Sequence
<220> FEATURE:
<223> OTHER INFORMATION: oligonucleotide primer ZC38953

<400> SEQUENCE: 14
ccgaattcct tatcgaggtg gtcttgagct                              30

<210> SEQ ID NO 15
<211> LENGTH: 17
<212> TYPE: DNA
<213> ORGANISM: Artificial Sequence
<220> FEATURE:
<223> OTHER INFORMATION: oligonucleotide primer ZC447

<400> SEQUENCE: 15
taacaatttc acacagg                                            17

<210> SEQ ID NO 16
<211> LENGTH: 18
<212> TYPE: DNA
<213> ORGANISM: Artificial Sequence
<220> FEATURE:
<223> OTHER INFORMATION: oligonucleotide primer ZC976

<400> SEQUENCE: 16
cgttgtaaaa cgacggcc                                           18

<210> SEQ ID NO 17
<211> LENGTH: 69
<212> TYPE: DNA
<213> ORGANISM: Artificial Sequence
<220> FEATURE:
<223> OTHER INFORMATION: oligonucleotide primer ZC40105

<400> SEQUENCE: 17
ctagaaataa ttttgtttaa ctttaagaag gagatatata tatgtcatac catgaccgga    60
agtcaaaag                                                     69

<210> SEQ ID NO 18
<211> LENGTH: 47
<212> TYPE: DNA
<213> ORGANISM: Artificial Sequence
<220> FEATURE:
<223> OTHER INFORMATION: oligonucleotide primer ZC40369

<400> SEQUENCE: 18
cttccacgag ggaccaatga tgacccagaa cctgatgacc cggatcc            47

<210> SEQ ID NO 19
<211> LENGTH: 47
<212> TYPE: DNA
<213> ORGANISM: Artificial Sequence
<220> FEATURE:
<223> OTHER INFORMATION: oligonucleotide primer ZC40368

<400> SEQUENCE: 19
ggatccgggt catcaggttc tgggtcatca ttggtccctc gtggaag            47

<210> SEQ ID NO 20
<211> LENGTH: 65
<212> TYPE: DNA
<213> ORGANISM: Artificial Sequence

```
<220> FEATURE:
<223> OTHER INFORMATION: oligonucleotide primer ZC40106

<400> SEQUENCE: 20
tctgtatcag gctgaaaatc ttatctcatc cgccaaaaca ttatcgaggt ggtcttgagc     60
tgcag                                                                65

<210> SEQ ID NO 21
<211> LENGTH: 40
<212> TYPE: DNA
<213> ORGANISM: Artificial Sequence
<220> FEATURE:
<223> OTHER INFORMATION: oligonucleotide primer ZC26109

<400> SEQUENCE: 21
taggtgtttt cacgagcact tcaccaacaa ggaccataga                           40

<210> SEQ ID NO 22
<211> LENGTH: 40
<212> TYPE: DNA
<213> ORGANISM: Artificial Sequence
<220> FEATURE:
<223> OTHER INFORMATION: oligonucleotide primer ZC26110

<400> SEQUENCE: 22
gtatcaggct gaaaatctta tctcatccgc caaaacaccc                           40

<210> SEQ ID NO 23
<211> LENGTH: 60
<212> TYPE: DNA
<213> ORGANISM: Artificial Sequence
<220> FEATURE:
<223> OTHER INFORMATION: oligonucleotide primer ZC26106

<400> SEQUENCE: 23
tcaccaacaa ggaccataga ttatgaaaca ccagcatcaa caccaacatc agcaccagca     60

<210> SEQ ID NO 24
<211> LENGTH: 60
<212> TYPE: DNA
<213> ORGANISM: Artificial Sequence
<220> FEATURE:
<223> OTHER INFORMATION: oligonucleotide primer ZC26113

<400> SEQUENCE: 24
tctcatccgc caaaacaccc gggctgctga tgctggtgct gatgttggtg ttgatgctgg     60

<210> SEQ ID NO 25
<211> LENGTH: 47
<212> TYPE: DNA
<213> ORGANISM: Artificial Sequence
<220> FEATURE:
<223> OTHER INFORMATION: oligonucleotide primer ZC26547

<400> SEQUENCE: 25
aacaaggacc atagattatg aaacaccagc atcaacacca acatcag                   47

<210> SEQ ID NO 26
<211> LENGTH: 50
<212> TYPE: DNA
<213> ORGANISM: Artificial Sequence
<220> FEATURE:
<223> OTHER INFORMATION: oligonucleotide primer ZC27864

<400> SEQUENCE: 26
```

```
aaacaccagc atcaacacca acatcagcac cataaggagg agtagcatat        50
```

<210> SEQ ID NO 27
<211> LENGTH: 50
<212> TYPE: DNA
<213> ORGANISM: Artificial Sequence
<220> FEATURE:
<223> OTHER INFORMATION: oligonucleotide primer ZC27865

<400> SEQUENCE: 27

```
atcttatctc atccgccaaa acacccgggc atatgctact cctccttatg        50
```

<210> SEQ ID NO 28
<211> LENGTH: 50
<212> TYPE: DNA
<213> ORGANISM: Artificial Sequence
<220> FEATURE:
<223> OTHER INFORMATION: oligonucleotide primer ZC29740

<400> SEQUENCE: 28

```
ttgacaatta atcatcggct cgtataatgt gtggaattgt gagcggataa        50
```

<210> SEQ ID NO 29
<211> LENGTH: 42
<212> TYPE: DNA
<213> ORGANISM: Artificial Sequence
<220> FEATURE:
<223> OTHER INFORMATION: oligonucleotide primer ZC29741

<400> SEQUENCE: 29

```
tctgatttaa tctgtatcag gctgaaaatc ttatctcatc cg                42
```

<210> SEQ ID NO 30
<211> LENGTH: 60
<212> TYPE: DNA
<213> ORGANISM: Artificial Sequence
<220> FEATURE:
<223> OTHER INFORMATION: oligonucleotide primer ZC29737

<400> SEQUENCE: 30

```
gtggaattgt gagcggataa caattcccct ctagaaataa ttttgtttaa ctttaagaag   60
```

<210> SEQ ID NO 31
<211> LENGTH: 65
<212> TYPE: DNA
<213> ORGANISM: Artificial Sequence
<220> FEATURE:
<223> OTHER INFORMATION: oligonucleotide primer ZC29735

<400> SEQUENCE: 31

```
tgaaaatctt atctcatccg ccaaaacacc cgggatatat atctccttct taaagttaaa   60
caaaa                                                              65
```

<210> SEQ ID NO 32
<211> LENGTH: 881
<212> TYPE: DNA
<213> ORGANISM: Artificial Sequence
<220> FEATURE:
<223> OTHER INFORMATION: pTAP339 insert

<400> SEQUENCE: 32

```
ttgacaatta atcatcggct cgtataatgt gtggaattgt gagcggataa caattcccct   60
ctagaaataa ttttgtttaa ctttaagaag gagatatata tatgtcatac catgaccgga  120
agtcaaaagt tgacctggat aggctcaatg atgatgccaa gcgttacagt tgcactccca  180
```

```
ggaattactc ggtcaatata agagaagagc tgaagttggc caatgtggtc ttctttccac      240
gttgcctcct cgtgcagcgc tgtggaggaa attgtggctg tggaactgtc aactggaggt      300
cctgcacatg caattcaggg aaaaccgtga aaaagtatca tgaggtatta cagtttgagc      360
ctggccacat caagaggagg ggtagagcta agaccatggc tctagttgac atccagttgg      420
atcaccatga acgatgcgat tgtatctgca gctcaagacc acctcgagga tccgggtcat      480
caggttctgg gtcatcattg gtccctcgtg aagctcata ccatgaccgg aagtcaaaag       540
ttgacctgga taggctcaat gatgatgcca agcgttacag ttgcactccc aggaattact      600
cggtcaatat aagagaagag ctgaagttgg ccaatgtggt cttctttcca cgttgcctcc      660
tcgtgcagcg ctgtggagga aattgtggct gtggaactgt caactggagg tcctgcacat      720
gcaattcagg gaaaaccgtg aaaagtatc atgaggtatt acagtttgag cctggccaca       780
tcaagaggag gggtagagct aagaccatgg ctctagttga catccagttg gatcaccatg      840
aacgatgcga ttgtatctgc agctcaagac cacctcgata a                          881
```

<210> SEQ ID NO 33
<211> LENGTH: 10
<212> TYPE: PRT
<213> ORGANISM: Artificial Sequence
<220> FEATURE:
<223> OTHER INFORMATION: peptide linker

<400> SEQUENCE: 33

Ser Gly Ser Gly Ser Ser Gly Ser Gly Ser
1               5                   10

<210> SEQ ID NO 34
<211> LENGTH: 345
<212> TYPE: PRT
<213> ORGANISM: Homo sapiens

<400> SEQUENCE: 34

Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
            35                  40                  45

Ile Ile Thr Val Ser Thr Asn Gly Ser Ile His Ser Pro Arg Phe Pro
        50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

-continued

```
Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
        210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
            275                 280                 285

His Asn Cys Asn Glu Cys Gln Cys Val Pro Ser Lys Val Thr Lys Lys
        290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345
```

MATERIALS AND METHODS FOR PREPARING DIMERIC GROWTH FACTORS

CROSS-REFERENCE TO RELATED APPLICATION

This application claims the benefit under 35 U.S.C. 119(e) of provisional application Ser. No. 60/355,882, filed Feb. 11, 2002, which is incorporated herein by reference in its entirety.

BACKGROUND OF THE INVENTION

In multicellular animals, cell growth, differentiation, and migration are controlled by polypeptide growth factors. These growth factors play a role in both normal development and pathogenesis, including the development of solid tumors. Polypeptide growth factors influence cellular events by binding to cell-surface receptors, many of which are tyrosine kinases. Binding initiates a chain of signalling events within the cell, which ultimately results in phenotypic changes, such as cell division, protease production, and cell migration.

Growth factors can be classified into families on the basis of structural similarities. One such family, the PDGF (platelet derived growth factor) family, is characterized by a dimeric structure stabilized by disulfide bonds. This family includes the PDGFs, the placental growth factors (PlGFs), and the vascular endothelial growth factors (VEGFs). The PDGFs are a group of disulfide-bonded, dimeric proteins. Four PDGF polypeptide chains have been identified and named A, B, C, and D chain. The A and B chains forms dimers with themselves and each other, resulting in AA, BB, and AB dimers. See, in general, Ross et al., *Cell* 46:155–169, 1986 and Hart et al., *Biochem.* 29:166–172, 1990. Recombinant forms of these proteins, including truncated and substitutional variants, are disclosed in U.S. Pat. Nos. 4,801,542; 4,845,075; 4,849,407; 4,889,919; and 5,895,755. Two additional PDGF polypeptides, designated C and D, have been described. See, WIPO Publication WO 00/34474; WIPO Publication WO 00/66736; Bergsten et al., *Nature Cell Biol.* 3:512–516, 2001; LaRochelle et al., *Nature Cell Biol.* 3:517–521, 2001; and Uutela et al., *Circulation* 103: 2242–2247, 2001. PDGF-C is also known as "zvegf3" (WO 00/34474), and PDGF-D is also known as "zvegf4" (WO 00/66736).

PDGF-C and PDGF-D have a multidomain structure that comprises an amino-terminal CUB domain and a carboxyl-terminal growth factor domain joined by an interdomain region of approximately 70 amino acid residues. The growth factor domain of PDGF-D, which comprises approximately residues 250–370 of human PDGF-D (SEQ ID NO:2), is characterized by an arrangement of cysteine residues and beta strands that is characteristic of the "cystine knot" structure of the PDGF family. The CUB domain shows sequence homology to CUB domains in the neuropilins (Takagi et al., *Neuron* 7:295–307, 1991; Soker et al., *Cell* 92:735–745, 1998), human bone morphogenetic protein-1 (Wozney et al., *Science* 242:1528–1534, 1988), porcine seminal plasma protein and bovine acidic seminal fluid protein (Romero et al., *Nat. Struct. Biol.* 4:783–788, 1997), and *Xenopus laevis* tolloid-like protein (Lin et al., *Dev. Growth Differ.* 39:43–51, 1997).

PDGF-C and PDGF-D form homodimeric proteins (PDGF-CC and PDGF-DD) that are proteolytically cleaved to produce the active species, in each case a growth factor domain dimer. The active PDGF-DD protein binds to and activates the $\alpha/\alpha$, $\beta/\beta$ and $\alpha/\beta$ isoforms of the PDGF receptor. PDGF-DD dimers are mitogenic for a variety of mesenchymal cells (Bergsten et al., ibid.; LaRochelle et al., ibid.). In addition, mice infected with a PDGF-D adenovirus construct showed proliferation of endosteal bone (U.S. patent application Ser. No. 09/540,224).

Production of biologically active, recombinant PDGF-DD has been found to be problematic. See, for example, Bergsten et al., ibid. There is a need in the art for materials and methods for producing recombinant PDGF in economically feasible amounts.

DESCRIPTION OF THE INVENTION

Within one aspect of the present invention there is provided a fusion protein consisting of, from amino terminus to carboxyl terminus, a first PDGF-D growth factor domain polypeptide, a linker polypeptide, and a second PDGF-D growth factor domain polypeptide, wherein each of the first and second PDGF-D growth factor domain polypeptides consists of a sequence of amino acid residues as shown in SEQ ID NO:2 or SEQ ID NO:4 from amino acid x to amino acid y, wherein x is an integer from 246 to 258, inclusive, and y is an integer from 365–370, inclusive; wherein the linker polypeptide consists of from 11–40 amino acid residues; and wherein the fusion protein is optionally glycosylated. Within one embodiment of the invention, y is 370. Within other embodiments of the invention, x is 246, 248, or 250. Within another embodiment of the invention, x is 250 and y is 370. Within further embodiments of the invention, the linker polypeptide consists of from 12 to 20 amino acid residues or from 14 to 16 amino acid residues. Within still other embodiments of the invention, the linker polypeptide does not contain Lys or Arg, the linker polypeptide does not contain Cys, or the linker polypeptide does not contain Pro. Within a further embodiment of the invention, the linker polypeptide comprises a proteolytic cleavage site. Within another embodiment of the invention, the first and second PDGF-D growth factor domain polypeptides are joined by at least one interchain disulfide bond.

Within a second aspect of the invention there is provided a polynucleotide encoding a fusion protein as disclosed above. Within one embodiment, the polynucleotide further encodes a secretory peptide operably linked to the fusion protein. Within another embodiment, the polynucleotide is DNA.

Within a third aspect of the invention there is provided an expression vector comprising the following operably linked elements: a transcription promoter; a DNA segment encoding a fusion protein as disclosed above; and a transcription terminator.

Within a fourth aspect of the invention there is provided a cultured cell into which has been introduced an expression vector as disclosed above.

Within a fifth aspect of the invention there is provided a method of making a protein comprising the steps of culturing a cell as disclosed above in a culture medium whereby the DNA segment is expressed and the fusion protein is produced, and recovering the fusion protein. Within one embodiment, the cell is a eukaryotic cell, the DNA segment encodes a secretory peptide operably linked to the fusion protein, and the fusion protein is secreted from the cell and is recovered from the culture medium. Within a related embodiment, the recovered fusion protein comprises at least one disulfide bond joining the first PDGF-D growth factor domain polypeptide to the second PDGF-D growth factor domain polypeptide. Within another embodiment, the linker polypeptide comprises a proteolytic cleavage site and, subsequent to the recovering step, the fusion protein is proteolytically cleaved at the cleavage site. Within a further embodiment, the linker polypeptide comprises a proteolytic cleavage site, the cell produces a protease that cleaves at the cleavage site, and the fusion protein is cleaved by the protease within the cell during secretion. Within an additional embodiment, the cell is a prokaryotic cell.

Within a sixth aspect of the invention there is provided a protein produced according to the method disclosed above.

These and other aspects of the invention will become evident upon reference to the following detailed description of the invention.

As used herein, a "biologically active" PDGF-DD protein is a PDGF-DD protein that binds to cell-surface PDGF receptors ($\alpha/\alpha$, $\alpha/\beta$, or $\beta/\beta$ receptors) and thereby stimulates a cellular response such as migration, differentiation, or mitosis.

The phrase "a cultured cell into which has been introduced an expression vector" includes cells that have been physically manipulated to contain the vector, as well as progeny of the manipulated cells when the progeny also contain the vector.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated polynucleotide molecules of the present invention are free of other genes with which they are ordinarily associated, but may include naturally occurring 5' and 3' untranslated regions such as promoters and terminators. The identification of associated regions will be evident to one of ordinary skill in the art (see, for example, Dynan and Tijan, *Nature* 316:774–778, 1985).

An "isolated" polypeptide or protein is a polypeptide or protein that is found in a condition other than its native environment, such as apart from blood and animal tissue. Within one embodiment, the isolated polypeptide or protein is substantially free of other polypeptides or proteins, particularly other polypeptides or proteins of animal origin. Isolated polypeptides or proteins may be provided in a highly purified form, i.e. greater than 95% pure or greater than 99% pure. When used in this context, the term "isolated" does not exclude the presence of the same polypeptide or protein in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "PDGF-D polypeptide" is used herein to denote a polypeptide comprising the core growth factor domain of a PDGF-D (e.g., residues 258–365 of human zvegf4 (SEQ ID NO:2) or mouse zvegf4 (SEQ ID NO:4)). A PDGF-D polypeptide may further comprise one or more additional amino acids derived from the full-length PDGF-D polypeptide chain or from a heterologous polypeptide. Using methods known in the art, PDGF-D polypeptides can be prepared in a variety of forms, including glycosylated or non-glycosylated, pegylated or non-pegylated, with or without an initial methionine residue, and as fusion polypeptides. PDGF-D polypeptides may be in the form of monomers or disulfide-bonded dimers.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

All references cited herein are incorporated by reference in their entirety.

The present invention provides dimeric PDGF proteins and materials and methods for making them. The invention is described herein in terms of the representative PDGF-DD dimer. However, those skilled in the art will recognize that the materials and methods of the invention are equally applicable to the production of other PDGF dimers, including, for example, PDGF AA, AB, BB, and CC dimers, and that these dimers, and materials and methods for making them, are within the scope of the invention. Moreover, those skilled in the art will recognize that the invention is not limited to the wild-type sequenes of the PDGF polypeptides, but comprehends the use of variant sequences. PDGF polypeptides and variants thereof, included substituted and truncated variants, are known in the art. See, for example, U.S. Pat. Nos. 4,801,542; 4,845,075; 4,849,407; 4,889,919; and 5,895,755; WIPO Publication WO 00/34474; Betsholtz et al., *Nature* 320:695–699, 1986; Tong et al., *Nature* 328: 619–621, 1987; and Collins et al., *Nature* 320:621–624, 1987.

A representative human PDGF-D polypeptide sequence (primary translation product) is shown in SEQ ID NO:2, and a representative mouse PDGF-D polypeptide sequence is shown in SEQ ID NO:4. DNAs encoding these polypeptides are shown in SEQ ID NOS: 1 and 3, respectively. Those skilled in the art will recognize that these sequences represent single alleles of the respective human and mouse genes, and that allelic variation is expected to exist. Analysis of the amino acid sequence shown in SEQ ID NO:2 indicates that residues 1 to 18 form a secretory peptide. The primary translation product also includes a CUB domain extending from approximately residue 52 to approximately residue 179; a propeptide-like sequence extending from approximately residue 180 to either residue 245, residue 249 or residue 257 with four potential cleavage sites, including monobasic sites at residue 245 and residue 249, a dibasic site at residues 254–255, and a target site for furin or a furin-like protease at residues 254–257; and the carboxyl-terminal growth factor domain disclosed above. Protein produced by expressing the full-length DNA in a baculovirus expression system showed cleavage between residues 249 and 250, as well as longer species with amino termini at residues 19 and 35. Cleavage of full-length PDGF-DD dimer with plasmin resulted in activation of the protein. By Western analysis, a band migrating at approximately the same size as the growth factor domain was observed. A matched, uncleaved, full-length PDGF-DD sample demonstrated no activity.

While not wishing to be bound by theory, it is believed that the PDGF-D growth factor domain forms anti-parallel dimers, as do the PDGF A and B polypeptides. It is also believed that the two PDGF-D polypeptides are joined by at least one interchain disulfide bond.

The materials and methods of the present invention resulted in enhanced production of PDGF-D growth factor domain dimers. Expression of full-length PDGF-D and the isolated growth factor domain in a baculovirus system resulted in low levels of biologically active protein. Increasing selective pressure did not produce satisfactory expression levels. When a truncated PDGF-D polypeptide beginning at Arg-250 of SEQ ID NO:2 was produced in cultured insect and mammalian cells, a substantial portion of the secreted product was in an inactive, monomeric form. However, the present inventors increased the proportion of biologically active PDGF-DD through the use of a fusion protein. It is believed that this increase was at least in part due to improved dimerization.

Within the present invention, biologically active PDGF-DD proteins comprising two PDGF-D polypeptides are produced by expressing, in a cultured host cell, a polynucleotide encoding a fused polypeptide chain consisting of, from amino to carboxyl terminus, a first PDGF-D growth factor domain polypeptide, a linker polypeptide, and a second PDGF-D growth factor domain polypeptide. Depending upon the type of host cell, the protein is produced as a linear polypeptide lacking disulfide bonds or with the first and second PDGF-D growth factor domain polypeptides joined by at least one disulfide bond. If the protein is produced as a linear polypeptide, the desired disulfide bonds can be formed according to routine methods as disclosed in more detail below.

Within the proteins of the present invention, the PDGF-D growth factor domain polypeptide consists of a sequence of amino acid residues as shown in SEQ ID NO:2 or SEQ ID NO:4 from amino acid x to amino acid y, wherein x is an integer from 246 to 258, inclusive, and y is an integer from 365–370, inclusive. Thus, the PDGF-D growth factor domain polypeptide may consist of, for example, residues 246–370 of SEQ ID NO:2, residues 247–370 of SEQ ID NO:2, residues 248–370 of SEQ ID NO:2, residues 249–370 of SEQ ID NO:2, residues 250–370 of SEQ ID NO:2, residues 251–370 of SEQ ID NO:2, residues 252–370 of SEQ ID NO:2, residues 253–370 of SEQ ID NO:2, residues 254–370 of SEQ ID NO:2, residues 255–370 of SEQ ID NO:2, residues 256–370 of SEQ ID NO:2, residues 257–370 of SEQ ID NO:2, or residues 258–370 of SEQ ID NO:2. Within other embodiments of the invention the PDGF-D growth factor domain polypeptide has an amino-terminus of one of the polypeptides disclosed above, and a carboxyl terminus at residue 365 of SEQ ID NO:2, residue 366 of SEQ ID NO:2, residue 367 of SEQ ID NO:2, residue 368 of SEQ ID NO:2. or residue 369 of SEQ ID NO:2. Within other embodiments the PDGF-D growth factor domain polypeptide consists of the corresponding residues of SEQ ID NO:4.

The PDGF A-chain growth factor domain has an amino terminus at an amino acid residue within residues 1–9, inclusive, of the mature A-chain sequence (U.S. Pat. No. 4,849,407). Within certain embodiments of the invention, the amino termius is within residues 1–5, inclusive. The PDGF A-chain growth factor domain has a carboxyl terminus at an amino acid residue within residues 96–104 of the mature sequence.

The PDGF B-chain growth factor domain has an amino terminus at an amino acid residue within residues 1–15, inclusive, of the mature B-chain sequence (U.S. Pat. No. 4,849,407). Within certain embodiments of the invention, the amino termius is within residues 1–11, inclusive. The PDGF B-chain growth factor domain has a carboxyl terminus at an amino acid residue within residues 102–109 of the mature sequence.

The PDGF C-chain growth factor domain has an amino terminus within residues 226–236, inclusive, of SEQ ID NO:34, and a carboxyl terminus within residues 340–345, inclusive, of SEQ ID NO:34.

In general, the linker polypeptide is designed to provide, upon folding of the fused polypeptide chain, a distance of at least 35 Å between the carboxyl terminus of the first PDGF-D growth factor domain polypeptide and the amino terminus of the second PDGF-D growth factor domain polypeptide. In practice, the linker polypeptide will ordinarily span more than 35 Å to more readily accommodate the three-dimensional structure of the molecule. Hence, linkers spanning 40 Å or more, for example 45 Å or 50 Å, are preferred. Calculation of the effective length of a polypeptide in solution is routine in the art. See, for example, Creighton, *Proteins: Structures and Molecular Properties*, $2^{nd}$ edition, W. H. Freeman and Company, 1993, Chapter 5. The linker polypeptide consists of at least 11 amino acid residues and may be as long as 40 residues, commonly not more than 25 residues, and ordinarily not more than 20 residues in length. Thus, the present invention includes, without limitation, the use of linker polypeptides of 12, 13, 14, 15, 16, 17, 18, 19, and 20 residues, with linkers of 14–16 residues particularly preferred.

The linker polypeptide should have an overall hydrophilic character and be non-immunogenic and flexible. As used herein, a "flexible" linker is one that lacks a substantially stable higher-order conformation in solution. Areas of local charge are to be avoided. In general, small, polar, and hydrophilic residues are preferred, and bulky and hydrophobic residues are undesirable. If the linker polypeptide includes charged residues, they will ordinarily be positioned so as to provide a net neutral charge within a small region of the polypeptide. It is therefore preferred to place a charged residue adjacent to a residue of opposite charge. In general, preferred residues for inclusion within the linker polypeptide include Gly, Ser, Ala, Thr, Asn, and Gln; more preferred residues include Gly, Ser, Ala, and Thr; and the most preferred residues are Gly and Ser. In general, Phe, Tyr, Trp, Cys, Pro, Leu, Ile, Lys, and Arg residues will be avoided, Cys residues due to their potential for formation of unwanted disulfide bonds, Pro residues due to their hydrophobicity and lack of flexibility, and Lys and Arg residues due to potential immunogenicity. However, these less desirable residues may be included to provide a specific proteolytic cleavage site as disclosed below. Within certain embodiments of the invention the linker polypeptide comprises a proteolytic cleavage site to facilitate removal of the peptide link between the first and second PDGF-D growth factor domain polypeptides. Exemplary proteolytic cleavage sites include sequences cleaved by plasmin, thrombin, factor Xa, enterokinase, furin, and rhinovirus 3C protease. The use of these and other proteases to cleave fusion proteins is known in the art. See, for example, Rubinstein et al., WO 00/61768; van de Ven et al., U.S. Pat. No. 5,935,815; and Fischer et al., U.S. Pat. No. 6,010,844. Thrombin cleaves after the dipeptide sequence Arg-Pro or Pro-Arg. Enterokinase cleaves after the pentapeptide sequence Asp-Asp-Asp-Asp-Lys (SEQ ID NO:5). Factor Xa cleaves after the sequence Ile-Glu-Gly-Arg (SEQ ID NO:6). Plasmin cleaves after the sequence Arg-Pro. The human rhinovirus 3C protease cleaves Gln-Gly peptide bonds, such as in the sequence Leu-Glu-Val-Leu-Phe-Gln-Gly-Pro (SEQ ID NO:7). Furin cleaves after Arg-Xaa-Lys/Arg-Arg (SEQ ID NO:8). Exemplary linkers are those having two repeats of the structure Ser-Gly-Ser-Gly-Ser (SEQ ID NO:9) in combination with a proteolytic cleavage site, such as the linker Ser-Gly-Ser-Gly-Ser-Gly-Ser-Gly-Ser-Leu-Val-Pro-Arg-Gly-Ser (SEQ ID NO:10), which includes a thrombin cleavage site.

The present invention also provides polynucleotide molecules, including DNA and RNA molecules, that encode the PDGF-D polypeptides disclosed above. The polynucleotides of the present invention include both single-stranded and double-stranded molecules. A representative DNA sequence encoding human PDGF-D is set forth in SEQ ID NO:1, and a representative DNA sequence encoding mouse PDGF-D is set forth in SEQ ID NO:3. Additional DNA sequences encoding PDGF-D polypeptides can be readily generated by those of ordinary skill in the art based on the genetic code. Counterpart RNA sequences can be generated by substitution of U for T. Those skilled in the art will readily recognize that, in view of the degeneracy of the genetic code, considerable sequence variation is possible among polynucleotide molecules encoding PDGF-D polypeptides.

Methods for preparing DNA and RNA are well known in the art. Complementary DNA (cDNA) clones are prepared from RNA that is isolated from a tissue or cell that produces large amounts of PDGF-D RNA. Such tissues and cells are identified by Northern blotting (Thomas, *Proc. Natl. Acad. Sci. USA* 77:5201, 1980), and include heart, pancreas, stomach, and adrenal gland. Total RNA can be prepared using guanidine HCl extraction followed by isolation by centrifugation in a CsCl gradient (Chirgwin et al., *Biochemistry* 18:52–94, 1979). Poly $(A)^+$ RNA is prepared from total RNA using the method of Aviv and Leder (*Proc. Natl. Acad. Sci. USA* 69:1408–1412, 1972). Complementary DNA is prepared from poly$(A)^+$ RNA using known methods. In the alternative, genomic DNA can be isolated. For some applications (e.g., expression in transgenic animals) it may be advantageous to use a genomic clone, or to modify a cDNA clone to include at least one genomic intron. Methods for identifying and isolating cDNA and genomic clones are well known and within the level of ordinary skill in the art, and include the use of the sequences disclosed herein, or parts thereof, for probing or priming a library. Polynucleotides encoding PDGF-D polypeptides are identified and isolated by, for example, hybridization or polymerase chain reaction ("PCR", Mullis, U.S. Pat. No. 4,683,202). Expression libraries can be probed with antibodies to PDGF-D, receptor fragments, or other specific binding partners.

The polynucleotides of the present invention can also be prepared by automated synthesis. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See, in general, Glick and Pasternak, *Molecular Biotechnology, Principles & Applications of Recombinant DNA*, ASM Press, Washington, D.C., 1994; Itakura et al., *Ann. Rev. Biochem.* 53: 323–356, 1984; and Climie et al., *Proc. Natl. Acad. Sci. USA* 87:633–637, 1990.

The proteins of the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms). Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, Green and Wiley and Sons, NY, 1993.

In general, a DNA sequence encoding a PDGF-D polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors, and other elements is a matter of routine design within the level of ordinary skill in the art. Many such elements are described in the literature and are available through commercial suppliers.

To direct a PDGF-D polypeptide into the secretory pathway of a host cell, a secretory signal sequence (also known as a leader sequence, prepro sequence or pre sequence) is provided in the expression vector. The secretory signal sequence may be that of a PDGF-D, or may be derived from another secreted protein (e.g., t-PA; see, U.S. Pat. No. 5,641,655) or synthesized de novo. The secretory signal sequence is operably linked to the PDGF-D DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the PDGF-D polypeptide, although certain signal sequences may be positioned elsewhere in the DNA sequence of interest (see, e.g., Welch et al., U.S. Pat. No. 5,037,743; Holland et al., U.S. Pat. No. 5,143,830).

Expression of PDGF-D polypeptides (including the fusion proteins of the present invention) via a host cell secretory pathway is expected to result in the production of dimeric proteins. Dimers may also be assembled in vitro upon incubation of PDGF-D polypeptides under suitable conditions. In general, in vitro assembly will include incubating the polypeptides under denaturing and reducing conditions followed by refolding and reoxidation of the polypeptides to form dimers. Recovery and assembly of proteins expressed in bacterial cells is disclosed below.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, 10801 University Blvd., Manassas, Va. USA under accession numbers 98669 and 98668, respectively, and derivatives of these vectors.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and Richardson, Ed., *Baculovirus Expression Protocols. Methods in Molecular Biology*, Humana Press, Totowa, N.J., 1995. Recombinant baculovirus can also be produced through the use of a transposon-based system described by Luckow et al. (*J. Virol.* 67:4566–4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971–976, 1990; Bonning et al., *J. Gen. Virol.* 75:1551–1556, 1994; and Chazenbalk and Rapoport, *J. Biol. Chem.* 270:1543–1549, 1995. In addition, transfer vectors can include an in-frame fusion with DNA encoding a polypeptide extension or affinity tag as disclosed above. Using techniques known in the art, a transfer vector containing a PDGF-D polypeptide-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses PDGF-D protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See, in general, Glick and Pasternak, *Molecular Biotechnology: Principles and Applications of Recombinant DNA*, ASM Press, Washington, D.C., 1994. See also, U.S. Pat. No. 5,300,435. Serum-free media are used to grow and maintain the cells. Suitable media formulations are known in the art and can be obtained from commercial suppliers. The cells are grown up from an inoculation density of approximately $2-5 \times 10^5$ cells to a density of $1-2 \times 10^6$ cells, at which time a recombinant viral stock is added at a multiplicity of infection (MOI) of 0.1 to 10, more typically near 3. Procedures used are generally described in available laboratory manuals (e.g., King and Possee, ibid.; O'Reilly et al., ibid.; Richardson, ibid.).

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459–3465, 1986; Cregg, U.S. Pat. No. 4,882,279; and Raymond et al., *Yeast* 14:11–23, 1998. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533. Production of recombinant proteins in *Pichia methanolica* is disclosed in U.S. Pat. No. 5,716,808; 5,736,383; 5,854,039; and 5,888,768.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zvegf4 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the:denaturant, such as by dialysis against a solution of urea and a combination of reduced and oxidized glutathione, followed by dialysis against a buffered saline solution.: In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

When the linker polypeptide comprises a proteolytic cleavage site, the PDGF-DD polypeptide can be cleaved within the host cell if the host cell produces a protease that cleaves at the cleavage site. If the host cell does not naturally produce the protease, it can be transfected to co-express the protease and the PDGF-DD polypeptide. See, for example, U.S. Pat. Nos. 5,648,254 and 5,935,815. Such intracellular cleavage of the PDGF-DD polypeptide will facilitate the secretion of a disulfide-bonded, dimeric protein.

The PDGF-DD proteins of the present invention that contain a cleavage site in the linker polypeptide can also be cleaved in vitro according to conventional methods. The use of proteases for processing recombinant proteins is routine in the art and includes the use of immobilized proteases. See, for example, U.S. Pat. No. 6,010,844. Specific reaction conditions are based on the protease to be used and will be adjusted to minimize unwanted proteolysis with the first polypeptide segment. In general, such parameters as reaction time and ratio of protease to substrate will be adjusted to obtain the desired result.

PDGF-DD proteins of the present invention are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Suitable chromatographic techniques include, without limitation, cation-exchange chromatography, hydrophobic interaction chromatography, size-exclusion chromatography, and affinity chromatography.

PDGF-DD proteins can be used wherever it is desired to stimulate the production of bone and/or connective tissue in both humans and non-human animals. Veterinary uses include use in domestic animals, including livestock and companion animals. Specific applications include, without limitation, fractures, including non-union fractures and fractures in patients with compromised healing, such as diabetics, alcoholics, and the aged; bone grafts; healing bone following radiation-induced osteonecrosis; implants, including joint replacements and dental implants; repair of bony defects arising from surgery, such as cranio-maxilofacial repair following tumor removal, surgical reconstruction following tramatic injury, repair of hereditary or other physical abnormalities, and promotion of bone healing in plastic surgery; treatment of periodontal disease and repair of other dental defects; treatment of bone defects following therapeutic treatment of bone cancers; increase in bone formation during distraction osteogenesis; treatment of joint injuries, including repair of cartilage and ligament; repair of joints that have been afflicted with osteoarthritis; tendon repair and re-attachment; treatment of osteoporosis (including age-related osteoporosis, post-menopausal osteoporosis, gluto-corticoid-induced osteoporosis, and disuse osteoporosis) and other conditions characterized by increased bone loss or decreased bone formation; elevation of peak bone mass in pre-menopausal women; and use in the healing of connective tissues associated with dura mater.

For pharmaceutical use, PDGF-DD proteins are formulated for local or systemic (particularly intravenous or subcutaneous) delivery according to conventional methods. In general, pharmaceutical formulations will include a PDGF-DD protein in combination with a pharmaceutically acceptable delivery vehicle. Delivery vehicles include biocompatible solid or semi-solid matrices, including powdered bone, ceramics, biodegradable and non-biodegradable synthetic polymers, and natural polymers; tissue adhesives (e.g., fibrin-based); aqueous polymeric gels; aqueous solutions; liposomes; ointments; and the like. These and other suitable vehicles are known in the art. Formulations may further include one or more additional growth factors, excipients, preservatives, solubilizers, buffering agents, albumin to prevent protein loss on vial surfaces, etc. Methods of formulation are well known in the art and are disclosed, for example, in *Remington: The Science and Practice of Pharmacy*, 20th ed., Gennaro et al., eds., Lippincott, Williams & Wilkins, Baltimore, 2000. The exact dose will be determined by the clinician according to accepted standards, taking into account the nature and severity of the condition to be treated, patient traits, etc. Determination of dose is within the level of ordinary skill in the art. Depending upon the route and method of administration, the protein may be administered in a single dose, as a prolonged infusion, or intermittently over an extended period. Intravenous administration will be by bolus injection or infusion over a typical period of one to several hours. Sustained release formulations can also be employed. In general, a therapeutically effective amount of zvegf4 is an amount sufficient to produce a clinically significant change in the treated condition, such as a clinically significant reduction in time required for fracture repair, a significant reduction in the volume of a void or other defect, a significant increase in bone density, a significant reduction in morbidity, or a significantly increased histological score.

PDGF-DD will ordinarily be used in a concentration of about 10 to 100 µg/ml of total volume, although concentrations in the range of 1 ng/ml to 1000 µg/ml may be used. For local application, such as for the regeneration of bone in a fracture or other bony defect, the protein will be applied in the range of 0.1–100 µg/cm² of wound area.

PDGF-DD proteins of the present invention can be used in combination with other growth factors and other therapeutic agents that have a positive effect on the growth of bone or connective tissue. Such growth factors include insulin-like growth factor 1 (IGF-1), PDGF, alpha and beta transforming growth factors (TGF-α and TGF-β), epidermal growth factor (EGF), bone morphogenetic proteins, leukemia inhibitory factor, and fibroblast growth factors. Other therapeutic agents include vitamin D, bisphosphonates, calcitonin, estrogens, parathyroid hormone, osteogenin, NaF, osteoprotegerin, and statins.

The invention is further illustrated by the following, non-limiting examples.

EXAMPLE 1

An expression vector, zVegf4[GFD]-FL2-TCS-zVegf4 [GFD]/pZBV37L, was prepared to express PDGF-DD protein in insect cells. The vector was designed to express two PDGF-D growth factor domain polypeptides (zvegf4 GFD) connected by a ten amino acid Ser-Gly-rich sequence and a six amino acid thrombin cleavage site (TCS) (SEQ ID NO:10). The protein was designated "zvegf4-sc-GFD."

An 830-bp fragment (designated zvegf4[GFD]-FL2-TCS-zvegf4[GFD]), containing BspEI and EcoRI restriction sites on the 5' and 3' ends, respectively, was generated by ligating two PCR-amplified fragments. The first fragment contained BspEI and BamHI sites on the 5' and 3' ends, respectively, and the second fragment contained Bam-HI and EcoRI sites on the 5' and 3' ends, respectively. The first fragment was generated by PCR amplification from a plasmid containing PDGF-D cDNA using primers zc38,955 (SEQ ID NO:11) and zc38,602 (SEQ ID NO:12). The second fragment was generated by PCR amplification from a plasmid containing PDGF-D cDNA using primers zc38,950 (SEQ ID NO:13) and zc38,953 (SEQ ID NO:14). The PCR reaction mixtures were incubated at 94° C. for 5 minutes followed by 35 cycles of 94° C. for 60 seconds, 58° C. for 120 seconds, and 72° C. for 180 seconds; held at at 72° C. for 10 minutes; followed by a 4° C. soak. The first fragment was digested with BspEI and BamHI, and the second fragment was digested with BamHI and EcoRI. The fragments were run on an agarose gel, excised, and purified using a spin column containing a silica gel membrane (QIAQUICK Gel Extraction Kit; Qiagen, Inc.). The resulting purified first and second fragments were ligated and electrophoresed on an agarose gel. A band corresponding to the combined sizes of the fragments was excised and purified using a spin column. The purified fragment was ligated into the vector pZBV37L, a modification of the PFASTBAC1 expression vector (Life Technologies, Gaithersburg, Md.) in which the polyhedron promoter had been removed and replaced with the late activating Basic Protein Promoter. Approximately 23 ng of the restriction digested zVegf4[GFD]-FL2-TCS-zVegf4 [GFD] insert and about 50 ng of the pZBV37L vector were ligated overnight at 16° C. The ligation mixture was transformed into *E. coli* host cells (ELECTROMAX DH12S; Life Technologies) by electroporation at 400 Ohms, 2V, and 25 µF in a 2-mm gap electroporation cuvette (BTX, Model No. 620). The transformed cells were diluted in 450 µl of SOC media (2% BACTO Tryptone (Difco Laboratories, Detroit, Mich.), 0.5% BACTO Yeast Extract (Difco Laboratories), 0.01 M NaCl, 1.5 mM KCl, 10 mM MgCl₂, 10 mM MgSO₄, and 20 mM glucose), and 100 µl of the dilution was plated onto LB plates containing 100 µg/ml ampicillin. Clones were analyzed by PCR, and three positive clones were selected to be outgrown and purified using a spin column (QIAPREP Spin Miniprep Kit; Qiagen, Inc.). The positive clones were also confirmed by sequencing. Two µl of each of the positive clones was transformed into 20 µl *E. coli* cells (MAX EFFICIENCY DH10BAC Competent Cells; Life Technologies) by heat shock for 45 seconds in a 42° C. heat block. The transformed cells were diluted in 980 tµl SOC media, and 100 µl was plated onto Luria Agar plates containing 50 µg/ml kanamycin, 7 µg/ml gentamicin, 10

μg/ml tetracycline, 40 μg/ml IPTG and 200 μg/ml halogenated indolyl-β-D-galactoside (bluo-gal). The plates were incubated for 48 hours at 37° C. A color selection was used to identify those cells having transposed viral DNA (referred to as a "bacmid"). Colonies that were white in color were picked for analysis and analyzed by PCR, and positive colonies (containing the desired bacmid) were selected for outgrowth and purified using a spin column. Clones were screened for the correct insert by amplifying DNA by PCR using primers to the transposable element in the bacmid (primers zc447 (SEQ ID NO:15) and zc976 (SEQ ID NO:16)). The PCR mixture was incubated at 94° C. for 5 minutes; 30 cycles of 94° C. for 60 seconds, 50° C. for 120 seconds, and 72° C. for 180 seconds; 72° C. for 10 min; followed by a 4° C. soak. The PCR product was run on a 1% agarose gel to check the insert size.

Clones having the correct insert size were used to transfect *Spodoptera frugiperda* (Sf9) cells. Sf9 cells were seeded at $1 \times 10^6$ cells per well in a 6-well plate and allowed to attach for 1 hour at 27° C. Ten microliters of bacmid DNA was diluted with 100 μl Sf-900 II SFM (Life Technologies). Twenty μl of a 3:1 (w/w) liposome formulation of the polycationic lipid 2,3-dioleyloxy-N-[2(sperminecarboxamido)ethyl]-N,N-dimethyl-1-propaniminium-trifluoroacetate and the neutral lipid dioleoyl phosphatidylethanolamine in membrane-filtered water (LIPOFECTAMINE™ Reagent; Life Technologies) was diluted with 100 μl Sf-900 II SFM. The bacmid DNA and lipid solutions were gently mixed and incubated 30–45 minutes at room temperature. The media from one well of cells was aspirated, and the cells were washed once with 2 ml fresh Sf-900 II SFM media. Eight hundred microliters of Sf-900 II SFM was added to the lipid-DNA mixture. The wash media was aspirated, and the DNA-lipid mixture was added to the cells. The cells were incubated at 27° C. overnight. The DNA-lipid mixture was aspirated, and 2 ml of Sf-900 II media was added to each plate. The plates were incubated at 27° C., 90% humidity, for 96 hours, after which the virus was harvested.

For the primary viral amplification, Sf9 cells were grown in 50 ml Sf-900 II SFM in a 125-ml shake flask to an approximate density of $1 \times 10^6$ cells/ml. They were then infected with 500 μl of the viral stock from the transfected 6-well plate and incubated at 27° C. for 3 days, after which the virus was harvested and titered.

EXAMPLE 2

A 50-ml culture of Sf9 cells at $2 \times 10^6$ cells/ml in a 125-ml shake flask at 27° C. was infected with 5 ml of primary amplified virus encoding human zvegf4-sc-GFD. The culture was harvested at 48 hours. The supernatant and a whole cell lysate were analyzed by western blotting. A band at 36 kDa, approximately the correct size, was seen in lanes corresponding to both supernatant and lysate samples.

Viral stocks were amplified in large scale. 1L shake flasks at 27° C. with $1 \times 10^6$ cells/ml were infected with the virus at a target MOI of 0.1 and incubated for 96 hours, at which time the supernatant was harvested and titered.

Large scale amplified virus was used to infect multiple 1-liter cultures of Sf9 cells at $2 \times 10^6$ cells/ml at an MOI of approximately 1 to 2. Supernatant was harvested at 48 hours.

EXAMPLE 3

Recombinant zvegf4-sc-GFD protein was recovered from conditioned culture media of baculovirus-infected insect cells. Ten 1-liter cultures were harvested, and the media were filtered using a 0.20 μm filter.

Protein was partially purified from the conditioned media by a combination of cation exchange, hydrophobic interaction, and size-exclusion chromatographies. Filtered culture medium (pH 6.3, conductivity 9 mS) was directly loaded onto a 50 ml cation-exchange column (POROS 50-HS; Applied Biosystems, Framingham, Mass.). The column was washed with ten column volumes (cv) of 96% starting buffer A (50 mM 2-(N-morpholino)ethanesulfonic acid (MES), pH 6.5) and 4% of Buffer B (50 mM MES, 2M NaCl, pH 6.6), and the bound protein was eluted with a 15-cv linear gradient to 100% buffer B, followed by 5 cv of 100% buffer B at 12 ml/min. Four-ml fractions were collected. Samples from the column were analyzed by SDS-PAGE with silver staining and western blotting for the presence of zvegf4-sc-GFD protein. Protein-containing fractions were pooled, mixed with ammonium sulfate pellet to a final concentration of 2 M, filtered through a 0.20 μm filtration unit (NALGENE), and loaded onto an 20-ml derivatized agarose column (Phenyl SEPHAROSE; Amersham Pharmacia Biotech). Proteins were eluted with a 3-cv linear gradient from 100% buffer C (50 mM sodium phosphate, 2 M ammonium sulfate, pH 7.0) to 40%, followed by a 10-cv linear gradient from 40% buffer C to 50 mM sodium phosphate, pH 7.0. Twelve-ml fractions were collected. The western blotting positive signal fractions were pooled and concentrated to 1 ml using Millipore concentrator-80 (Millipore) and loaded onto a 16×450 mm cross-linked dextran gel filtration column (SUPERDEX-75; Amersham Pharmacia Biotech) at 1 ml/min. Every two fractions containing purified zvegf4-sc-GFD were pooled and concentrated for assay.

Recombinant zvegf4-sc-GFD protein was analyzed by SDS-PAGE (Bis-Tris NUPAGE gel, 4–12%; Invitrogen, Carlsbad, Calif.) with silver staining (Fast Silver; Geno Tech, St. Louis, Mo.) and Western blotting using a monoclonal antibody to PDGF-D protein. Either the conditioned media or purified protein was electrophoresed using a commercially available blotting apparatus (NOVEX XCELL II mini-cell; Invitrogen) and transferred to nitrocellulose filters (0.2 μm; Invitrogen) at room temperature using a blot module (XCELL II; Invitrogen) with stirring according to directions provided in the instrument manual. The transfer was run at 500 mA for one hour in a buffer containing 25 mM Tris base, 200 mM glycine, and 20% methanol. The blots were then blocked with 10% non-fat dry milk in PBS for 10 minutes at room temperature. The blots were quickly rinsed, then the mouse primary antibody, diluted 1:2000 in PBS containing 2.5% non-fat dry milk, was added. The blots were incubated for two hours at room temperature or overnight at 4° C. with gentle shaking. Following the incubation, blots were washed three times for 10 minutes each in PBS, then labeled with a secondary antibody (goat anti-mouse IgG conjugated to horseradish peroxidase; Pierce Chemical Co., Rockford, Ill.) diluted 1:2000 in PBS containing 2.5% non-fat dry milk, and the blots were incubated for two hours at room temperature with gentle shaking. The blots were then washed three times, 10 minutes each, in PBS, then quickly rinsed with $H_2O$. The blots were developed using commercially available chemiluminescent substrate reagents (SUPERSIGNAL ULTRA reagents 1 and 2 mixed 1:1; reagents obtained from Pierce Chemical Co., Rockford, Ill.), and the signal was captured using commercially available software (LUMI-IMAGER LumiAnalyst 3.0; Boehringer Mannheim GmbH, Germany) for times ranging from 10 seconds to 5 minutes or as necessary.

The partially purified zvegf4-sc-GFD protein appeared as two bands on the silver-stained gel at about 32 and 20 kDa under both non-reducing conditions and reducing conditions. This result suggested existence of a two-tandem repeat form of zvegf4-sc-GFD and a zvegf4-GFD monomer possibly cleaved around the linker region of two zvegf4-GFD repeats. The partially purified protein was very active in a cell-based luciferase assay.

EXAMPLE 4

Rat stellate cells were grown in 96-well tissue clusters (FALCON; BD, Franklin Lakes, N.J.) in DMEM (Life Technologies, Gaithersburg, Md.) supplemented with 10% fetal bovine serum (Hyclone Laboratories, Inc., Logan, Utah). The next day, the medium was switched to serum-free medium by substituting 0.1% BSA (Fraction V, Sigma, St. Louis, Mo.) for serum. This medium also contained the adenoviral construct KZ136 that encodes a luciferase reporter mini-gene driven by SRE and STAT elements, at a 1000:1 multiplicity of infection (m.o.i.). After allowing 24 hours for the incorporation of the adenoviral construct into the cells, the media were changed and replaced with serum-free media +0.1% BSA that contained conditioned media (CM) from insect cells expressing zvegf4-sc-GFD or control cells at the indicated final concentration (Table, below). Four hours later the cells were lysed, and luciferase activity, denoting activation of the reporter gene, was determined in the lysate using a commercially available assay kit (obtained from Promega Corp., Madison, Wis.) and a luminescence reader (MICROLUMAT PLUS, Berthold Technologies, Bad Wildbad, Germany). Results (shown in the Table) were obtained as relative luciferase units (RLU) in the lysate, with a value of 1 assigned to the BSA control (no conditioned medium added to the cells).

TABLE

|  | Control CM | zvegf4-sc-GFD CM |
|---|---|---|
| BSA (Basal) | 1 | 1 |
| CM 1:30 dilution | 1 | 2 |
| CM 1:10 dilution | 1 | 2.6 |
| CM 1:3 dilution | 1 | 3.7 |

Conditioned media from insect cells that were transfected with the baculovirus expressing zvegf4-sc-GFD contained a protein that reacted with anti-PDGF-D antibodies and migrated at the right position on an SDS-protein gel (about 35 kDa non-reduced). By this method, protein concentration was estimated to be approximately 0.4 µg/ml. Conditioned media from untrasfected cells did not contain any moieties recognized by anti-PDGF-D antibodies.

Based on a standard curve using purified, recombinant PDGF-D-GFD protein (produced by expressing a DNA encoding the growth factor domain alone), the activity of the zvegf4-sc-GFD CM was roughly equivalent to 0.3 µg/ml of PDGF-D-GFD. This correlated with the concentration of this protein in the CM as determined by western blotting. It also showed that the single-chain GFD dimer was biologically active and that its activity weight per weight was comparable to that of PDGF-D-GFD.

EXAMPLE 5

A polynucleotide sequence of human zvegf4-sc-GFD was prepared. Two zvegf4 cDNA fragments were isolated by PCR from the template zVegf4[GFD]-FL2-TCS-zVegf4 [GFD]/pZBV37L (Example 1). For the first fragment, two primers were used to synthesize the first half of the single-chain molecule: (1) primer zc40,105 (SEQ ID NO:17), containing 41 bp of the vector flanking sequence and 25 bp corresponding to the amino terminus of the zvegf4 sequence; and (2) primer zc40,369 (SEQ ID NO:18), containing 100% homology internal to the zvegf4 template, of which 30 bp contained homology to fragment 2. The second fragment was synthesized using primer zc40,368 (SEQ ID NO:19), which contained 100% homology to the zvegf4 template, of which 30 bp contained homology to fragment 1, and primer zc40,106 (SEQ ID NO:20), which contained 40 bp of the vector flanking sequence and 25 bp corresponding to the carboxyl terminus of the zvegf4 sequence. The PCR reactions were run for 25 cycles of 94° C. for 30 seconds, 55° C. for 30 seconds, and 72° C. for 1 minute, followed by a 4° C. soak. Two µl of each of the 100-µl PCR reaction mixtures was run on a 1.0% agarose gel with 1×TBE buffer for analysis, and the expected bands of approximately 400 bp were seen. The remaining 98 µl of each PCR reaction mixture was precipitated with 200 µl of absolute ethanol for use in constructing an expression vector encoding the zvegf4-sc-GFD (pTAP339).

pTAP168 was generated by inserting a PCR-generated linker fragment into the SmaI site of pCZR239 via homologous recombination in yeast (*Saccharomyces cerevisiae*). (Plasmid pCZR239 was derived from the plasmids pRS316 (a *Saccharomyces cerevisiae* shuttle vector; Hieter and Sikorski, *Genetics* 122:19–27, 1989) and pMAL-c2 (obtained from New England Biolabs, Beverly, Mass.), an *E. coli* expression plasmid comprising the tac promoter driving MalE (encoding maltose binding protein) followed by a His tag, a thrombin cleavage site, a cloning site, and the rrnB terminator. Plasmid pCZR239 contains a kanamycin resistance gene in which the SmaI site has been destroyed, and has NotI and SfiI sites flanking the yeast CEN-ARS and URA3. sequences, facilitating their removal from the plasmid by digestion with NotI. pCZR239 further includes the original multiple cloning site of pMAL-c2.) The linker was prepared from 100 pmoles each of oligonucleotides zc26, 109 (SEQ ID NO:21) and zc26,110 (SEQ ID NO:22) and approximately 5 pmoles each of oligonucleotides zc26,106 (SEQ ID NO:23) and zc26,113 (SEQ ID NO:24). These oligonucleotides were combined by PCR for ten cycles of 94° C. for 30 seconds, 50° C. for 30 seconds, and 72° C. for 30 seconds, followed by a 4° C. soak. The PCR products were concentrated by precipitation with two times the volume of 100% ethanol. The precipitated product was resuspended in 10 µl of water and recombined with 1 µl of SmaI-cut pCZR239 by homologous recombination essentially as described below. The plates were left at room temperature for about 96 hours, then the Ura+ transformants from a single plate were resuspended in 1 ml H₂O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was transferred to a microcentrifuge tube containing 300 µl acid-washed glass beads, and 500 µl phenol-chloroform was added. The tube was vortexed for 1-minute intervals two or three times, followed by a 5-minute spin in a microcentrifuge at maximum speed. Three hundred microliters of the aqueous phase was transferred to a fresh tube, and the DNA was precipitated with 600 µl ethanol (EtOH), followed by centrifugation for 10 minutes at 4° C. The DNA pellet was resuspended in 100 µl H₂O. 1 µl of the DNA suspension was transformed into *E. coli* MC1061 (Casadaban et. al. *J. Mol. Biol.* 138:

179–207, 1980) as described below. Clones were screened by colony PCR using 20 pmoles each of oligonucleotides zc26,110 (SEQ ID NO:22) and zc26,109 (SEQ ID NO:21) and 10 μl of an LB-colony mixture as template. The reaction was run for 25 cycles of 94° C. for 30 seconds, 50° C. for 30 seconds, and 72° C. for 30 seconds, followed by a 4° C. soak. Clones displaying the correct size band on an agarose gel were subject to sequence analysis. The correct construct was designated pTAP168.

Plasmid pTAP186 was generated by inserting a PCR-generated linker fragment into the SmaI site of pTAP168 by homologous recombination. The linker was prepared from 100 pmoles each of oligonucleotides zc26,110 (SEQ ID NO:22) and zc26,547 (SEQ ID NO:25) and approximately 5 pmoles each of oligonucleotides zc27,864 (SEQ ID NO:26) and zc27,865 (SEQ ID NO:27). These oligonucleotides were combined by PCR for ten cycles of 94° C. for 30 seconds, 50° C. for 30 seconds, and 72° C. for 30 seconds, followed by a 4° C. soak. PCR products were concentrated by precipitation with two times the volume of 100% EtOH. The precipitated product was resuspended in 10 μl of water and recombined with 1 μl of SmaI-cut pTAP168 by homologous recombination essentially as described below. The plates were left at room temperature for about 96 hours, then the Ura+ transformants from a single plate were resuspended in 1 ml $H_2O$ and spun briefly to pellet the cells. The cell pellet was resuspended in 1 ml of lysis buffer, and the DNA was recovered and transformed into E. coli MC1061 essentially as disclosed above. One clone was screened by PCR as disclosed above using 20 pmoles each of oligonucleotides zc26,547 (SEQ ID NO:25) and zc26,110 (SEQ ID NO:22). Clones displaying the correct size band on an agarose gel were sequenced. The correct construct was designated pTAP186.

Plasmid pTAP238 was generated by inserting a PCR-generated linker into the SmaI site of pTAP186 by homologous recombination. The linker was prepared from 100 pmoles each of oligonucleotides zc29,740 (SEQ ID NO:28) and zc29,741 (SEQ ID NO:29), and approximately 5 pmoles each of oligonucleotides zc29,737 (SEQ ID NO:30) and zc29,735 (SEQ ID NO:31). These oligonucleotides were combined by PCR for ten cycles of 94° C. for 30 seconds, 50° C. for 30 seconds, and 72° C. for 30 seconds, followed by 4° C. soak. The resulting PCR products were concentrated by precipitation with two times the volume of 100% ethanol. The precipitated products were resuspended in 10 μl of water and recombined with 1 μl of SmaI-cut pTAP186 by homologous recombination essentially as described below. The yeast cells were plated and left at room temperature for about 72 hours, then the Ura+ transformants from a single plate were resuspended in 1 ml $H_2O$ and spun briefly to pellet the yeast cells. The cell pellet was resuspended in 0.5 ml of lysis buffer. DNA was recovered and transformed into E. coli MC1061 as disclosed above. Clones were screened by colony PCR as disclosed above using 20 pmoles each of oligonucleotides zc29,740 (SEQ ID NO:28) and zc29,741 (SEQ ID NO:29). Clones displaying the correct size band on an agarose gel were subject to sequence analysis. The correct plasmid was designated pTAP238.

One hundred microliters of competent yeast cells (S. cerevisiae) were combined with 10 μl of a mixture containing approximately 1 μl of each of the human zvegf4 fragments (PCR products) and 100 ng of SmaI-digested pTAP238 vector, and transferred to a 0.2-cm electroporation cuvette. The yeast/DNA mixture was electropulsed using instrument settings of 0.75 kV (5 kV/cm), infinite ohms, 25 μF, then 600 μl of 1.2 M sorbitol was added to the cuvette. The yeast was then plated in two 300-μl aliquots onto two —URA D (glucose-containing media lacking uracil) plates and incubated at 30° C. After about 48 hours, the Ura+ yeast transformants from a single plate were resuspended in 1 ml $H_2O$ and spun briefly to pellet the cells. The cell pellet was resuspended in 1 ml of lysis buffer. DNA was recovered as disclosed above. The DNA pellet was resuspended in 100 μl $H_2O$.

Forty μl of electrocompetent E. coli MC1061 cells were transformed with 1 μl of the yeast DNA. The cells were electropulsed at 2.0 kV, 25 μF and 400 ohms. Following electroporation, 0.6 ml SOC (2% BACTO Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added to the cells. The cells were allowed to recover at 37° C. for one hour, then were plated in one aliquot on LB+kanamycin plates (LB broth (Lennox), 1.8% BACTO Agar (Difco), 30 mg/L kanamycin).

Individual clones harboring the correct expression construct for human zvegf4-sc-GFD were identified by diagnostic digest of the plasmid DNA. Cells were grown in Super Broth II (Becton Dickinson) with 30 μg/ml of kanamycin overnight. The next day, the cells were harvested, and plasmid DNA was prepared using spin columns (QIAPREP Spin Miniprep Kit; Qiagen Inc., Valencia, Calif.). The DNA was then cut with NotI and XbaI. The clones with the correct restriction pattern were designated pTAP339 and sequenced. The polynucleotide sequence of single chain zvegf4 in pTAP339 is shown in SEQ ID NO:32.

Ten microliters of pTAP339 was cut with 2 microliters of NotI in 3 μl of a commercially available buffer (buffer 3; New England Biolabs) and 15 μl $H_2O$ for one hour at 37° C. 7 μl of the reaction mixture was combined with 2 microliters of 5×T4 DNA ligase buffer (Life Technologies, Gaithersburg, Md.) and 1 microliter of T4 DNA ligase and incubated at room termperature for one hour. One microliter of the ligation mixture was used to transform E. coli strain W3110 (ATCC 27325). The cells were electropulsed at 2.0 kV, 25 μF, and 400 ohms. Following electroporation, 0.6 ml SOC was added to the cells. The cells were grown at 37° C. for one hour, then plated in one aliquot on LB+kanamycin plates.

Individual colonies were picked and grown. Plasmid DNA was prepared using spin columns. The DNA was cut diagnostically with PvuII and HindIII to confirm the loss of yeast URA3 and CEN/ARS elements. This DNA was then transformed into E. coli ROSETTA competent cells (a BL21 derivative with pRARE; obtained from Novagen, Inc., Madison, Wis.) as described above. The cells were plated on 30 μg/ml kanaymcin and 35 μg/ml chloramphenicol due to the presence of pRARE.

An individual colony was picked. Cells were grown in SUPERBROTH II (Becton Dickinson) containing 30 μg/ml of kanamycin and 35 μg/ml chloramphenicol overnight. 100 μl of the overnight culture was used to inoculate 2 ml of fresh SUPERBROTH II containing 30 μg/ml kanamycin and 35 μg/ml chloramphenicol. Cultures were grown at 37° C. with shaking for about 2 hours in 15-ml conical tubes. One ml of the culture was induced with 1 mM IPTG. 2.25 hours later an equal volume of culture was mixed with 250 μl Thorner buffer (8M urea, 100 mM Tris pH7.0, 10% glycerol, 2 mM EDTA, 5% SDS) with 5% βME and dye. Samples were boiled for 5 minutes. Twenty-μl samples were loaded on a 4%–12% PAGE gel (NOVEX). Gels were run in 1×MES buffer. Expression was analyzed by Western blotting.

A NUPAGE 4–12% Bis Tris gel (Invitrogen) was run using 1×MES buffer. 2.5 µl of culture was loaded per lane (5 µl of culture and buffer). A zvegf4 standard (designated "A447F") was loaded as 25 ng and 50 ng. After the gel was run, the DNA was transferred to a nitrocellulose membrane via a NOVEX transfer box and protocol. The membrane was then blocked in 5% milk and TTBS (160 mM NaCl, 0.1% Tween 20, 20 mM Tris pH7.4) for 30 minutes. It was then incubated at room temperature with an anti-zvegf4 monoclonal antibody (designated E3501) as a 1:5000 dilution. The blot was then washed twice in TTBS for 5–10 minutes each. The washed blot was incubated at room temperature for one hour in a 1:5000 dilution of goat anti-mouse antibody (Bio-Rad Laboratories, Hercules, Calif.). The blot was then washed again in TTBS under the same conditions. The washed blot was then exposed to ECL reagent (Amersham) and exposed to film. Expression was seen in both uninduced and induced samples, presumably due to the known leakiness of the tac promoter.

What is claimed is:

1. An isolated fusion protein consisting of, from amino terminus to carboxyl terminus:
   a first PDGF-D growth factor domain polypeptide;
   a linker polypeptide; and
   a second PDGF-D growth factor domain polypeptide, wherein each of said first and second PDGF-D growth factor domain polypeptides consists of a sequence of amino acid residues as shown in SEQ ID NO:2 or SEQ ID NO:4 from amino acid x to amino acid y, wherein x is an integer from 246 to 258, inclusive, and y is an integer from 365 to 370, inclusive; wherein said linker polypeptide consists of from 11–40 amino acid residues; wherein said fusion protein is optionally glycosylated; and wherein said fusion protein is substantially free of other polypeptides or proteins.

2. The fusion protein of claim 1 wherein y is 370.

3. The fusion protein of claim 1 wherein x is 246, 248, or 250.

4. The fusion protein of claim 1 wherein x is 250 and y is 370.

5. The fusion protein of claim 1 wherein the linker polypeptide consists of from 12 to 20 amino acid residues.

6. The fusion protein of claim 1 wherein the linker polypeptide consists of from 14 to 16 amino acid residues.

7. The fusion protein of claim 1 wherein the linker polypeptide does not contain Lys or Arg.

8. The fusion protein of claim 1 wherein the linker polypeptide does not contain Cys.

9. The fusion protein of claim 1 wherein the linker polypeptide does not contain Pro.

10. The fusion protein of claim 1 wherein the linker polypeptide comprises a proteolytic cleavage site.

11. The fusion protein of claim 10 wherein the cleavage site is a plasmin cleavage site, a thrombin cleavage site, or a factor Xa cleavage site.

12. The fusion protein of claim 1 wherein the linker polypeptide comprises the amino acid sequence Ser-Gly-Ser-Gly-Ser-Ser-Gly-Ser-Gly-Ser (SEQ ID NO:33) and a proteolytic cleavage site.

13. The fusion protein of claim 1 wherein the first and second PDGF-D growth factor domain polypeptides are joined by at least one interchain disulfide bond.

14. An isolated fusion protein produced by a process comprising the steps of:
   (a) culturing a cell into which has been introduced an expression vector comprising the following operably linked elements:
      a transcription promoter,
      a DNA segment encoding the fusion protein of claim 1; and
      a transcription terminator,
      whereby the DNA segment is expressed and the fusion protein is produced; and
   (b) recovering the fusion protein, whereby the fusion protein is substantially free of other polypeptides or proteins.

* * * * *

UNITED STATES PATENT AND TRADEMARK OFFICE
CERTIFICATE OF CORRECTION

| | | |
|---|---|---|
| PATENT NO. | : 7,241,593 B2 | Page 1 of 1 |
| APPLICATION NO. | : 10/365095 | |
| DATED | : July 10, 2007 | |
| INVENTOR(S) | : Brian A. Fox et al. | |

It is certified that error appears in the above-identified patent and that said Letters Patent is hereby corrected as shown below:

Column 6, line 38, "SEQ ID NO:2. or residue" should be --SEQ ID NO:2, or residue--.
Column 11, line 67, remove ":" from "the:denaturant".
Column 12, line 2, remove ":" from "solution.: In".
Column 18, line 37, remove "." From "URA3.".
Column 19, line 62, "μ1" should be --μg--.
Claim 14, Column 44, line 50, "," should be --;--.

Signed and Sealed this

Fourth Day of September, 2007

JON W. DUDAS
*Director of the United States Patent and Trademark Office*